(12) United States Patent
Mafra-Neto et al.

(10) Patent No.: US 9,877,477 B2
(45) Date of Patent: Jan. 30, 2018

(54) COMPOSITIONS AND METHODS FOR REPELLING COFFEE BERRY BORER

(71) Applicant: ISCA Technologies, Inc., Riverside, CA (US)

(72) Inventors: Agenor Mafra-Neto, Riverside, CA (US); Josue Isaias Ponce, Whittier, CA (US); William H Urrutia, Riverside, CA (US); Carmem R. Bernardi, Riverside, CA (US); Rodrigo Oliveira Da Silva, Riverside, CA (US)

( * ) Notice: Subject to any disclaimer, the term of this patent is extended or adjusted under 35 U.S.C. 154(b) by 0 days.

(21) Appl. No.: 14/938,701

(22) Filed: Nov. 11, 2015

(65) Prior Publication Data

US 2016/0128324 A1 May 12, 2016

Related U.S. Application Data

(60) Provisional application No. 62/078,080, filed on Nov. 11, 2014.

(51) Int. Cl.
*A01N 31/06* (2006.01)
*A01N 35/06* (2006.01)
*A01N 25/18* (2006.01)

(52) U.S. Cl.
CPC ............ *A01N 35/06* (2013.01); *A01N 25/18* (2013.01)

(58) Field of Classification Search
None
See application file for complete search history.

(56) References Cited

U.S. PATENT DOCUMENTS

| 5,178,871 A | 1/1993 | Thill |
| 2007/0098750 A1 | 5/2007 | Bessette |
| 2010/0024279 A1 | 2/2010 | Plato et al. |
| 2010/0303940 A1 | 12/2010 | Enan |

OTHER PUBLICATIONS

Jaramillo et al., "Coffee Berry Borer Joins Bark Beetles in Coffee Klatch", Sep. 2013, vol. 8, Issue 9, pp. 1-15.*
Search report & written opinion of PCT/US15/60217, Authorized officer: Lee W. Young, dated Jan. 27, 2016.

* cited by examiner

*Primary Examiner* — Robert A Wax
*Assistant Examiner* — Randeep Singh
(74) *Attorney, Agent, or Firm* — Benjamin Diederich

(57) ABSTRACT

Compositions and methods for repelling coffee berry borer. The compositions contain a substrate and a semiochemical capable of affecting the coffee berry borer intermixed within the substrate. The semiochemical may be verbenone.

12 Claims, 2 Drawing Sheets

COMPOSITIONS AND METHODS FOR REPELLING COFFEE BERRY BORER

CROSS-REFERENCE TO RELATED APPLICATIONS

This application claims the benefit of U.S. Provisional Application No. 62/078,080, filed on Nov. 11, 2014, the teachings of which are expressly incorporated by reference.

STATEMENT RE: FEDERALLY SPONSORED RESEARCH/DEVELOPMENT

Not Applicable

BACKGROUND

1. Field of the Invention

The present invention relates to products, systems, and methods for controlling *Hypothenemus hampei* (coffee berry borer, CBB), the most economically important pest of coffee worldwide. More specifically, this invention relates to methods and systems for repelling CBB, for purposes of both population control and crop protection through the use of volatile semiochemicals with potent and varied behavioral effects. This semiochemical formulation can be employed in a broad range of means, including a monolithic repellent and repellent-impregnated rubber to be deployed in controlled areas, and a liquid formulation that can be amenable to spray application.

2. Background of the Invention

Chemicals existing within the environment that convey some form of information, known as semiochemicals, are used extensively by arthropods to communicate with each other and can be used in strategies for pest management.

The direct management of insect pests using semiochemicals for repellent approaches can provide excellent suppression of key coleopteran pests in agriculture and forestry. Large-scale implementation projects have yielded significant reductions in pesticide use while maintaining acceptably low crop-damage levels.

The coffee berry borer (CBB), *Hypothenemus hampei*, is the most economically significant pest of coffee worldwide, creating an estimated $500 million in losses annually. The beetle is native to Angola, however it extended its range throughout Africa during the early 20th century and has continued to do so since. It is believed that most invasions occur due to the importation of contaminated seeds, colloquially beans. Regardless of the mode of invasion, CBB has effectively extended its range to every major coffee producing country in the world, making landfall in the U.S. state of Hawaii in 2010.

The coffee industry has an estimated global economic value between $70 and $90 billion annually. Per pound retail prices for coffee can vary drastically depending on a variety of product parameters and the consumer market, for example per pound coffee prices within the U.S. market range from $2-$30 depending on the product. Due to these pricing variations the economic impact of CBB losses to some cultivars is substantially greater than others. When densities of CBB reach very high levels they can cause yield losses upwards of 35% with 100% of berries infested at harvest time, greater losses can occur if harvest is delayed. In addition to the direct loses, CBB damage can devalue coffee prices by 30-40%.

The CBB is such a destructive force in the coffee industry because the entire larval stage, and most of the adult stage, is spent within the coffee berry. Males never emerge from the berry, therefore the entire life cycle of a male CBB from development to mating is confined to the same coffee berry it hatched from. Female CBBs, on the other hand, remain within the coffee berry up until mating. Once mated, female CBBs attack immature and mature coffee berries. The attacking female bores a hole in the coffee berry and lays eggs amongst the seeds at a rate of 2 to 3 eggs per day for a period of 20 days. The larvae feed upon the seeds until they mature and mate, repeating the cycle. There is a 10:1 sex ratio favoring females; allowing for rapid proliferation throughout a coffee plantation. Further, as most of the life cycle occurs inside the berries, control strategies, both chemical and non-chemical, are greatly limited.

Because female CBB are able to fly and their lifespan allows for long durations of activity, (nearly six months under the correct environmental conditions) damage to developing berries can occur year round. Three types of damage have been reported due to CBB: 1) premature fall of young berries, 2) increased vulnerability of infested ripe berries to secondary infection, and 3) reduction in both yield and quality of coffee, reducing the profitability of the crop.

Historically, coffee farmers have relied on Endosulfan for the control of CBB, but as of April 2011, it has been phased out globally. Endosulfan is a highly toxic chemical that poses significant risk to human health by acting like an endocrine disruptor. It also poses high potential for bioaccumulation, which can negatively impact entire ecosystems surrounding coffee plantations. Further, CBB's life cycle makes it nearly inaccessible to most control measures. Coffee farmers have been left in an extremely difficult position where they must combat CBB with insecticides that have not yet been evaluated for effectiveness against CBB or labeled for use in coffee. Most insecticides used to date have proven ineffective for control of CBB.

Mycoinsecticide control products containing the spores of the fungus *Beauveria bassiana*, such as the EPA registered BOTANIGARD® ES (BioWorks, Victor, N.Y., US), have demonstrated the ability to reduce female oviposition rates and larvae production and increase CBB mortality. However, the product requires two separate applications, one mid and one late season, directly to the berries and surrounding ground cover, increasing planning and logistical requirements. Additionally, the product costs $60-490 per acre per application, making overall protection costly.

Alternatively, coffee farmers can employ various cultural control or hygiene approaches to reduce CBB populations within the plantation: removal of berries and trapping prior to and during fruit development, contained harvesting, and post harvest plantation sanitation.

Pruning fruit-producing trees is a necessity in maintaining a healthy and effective growth operation. Two methods of pruning exist within coffee farming: 1) pruning one or two verticals on the tree each year (the Kona method), or 2) pruning all the verticals on the tree in the same year every three to five years (the Beaumont-Fukunaga method). However, prior to pruning, any berries on the trees must be removed to ensure that they do not fall to the ground. Research has indicated berries not removed before pruning can result in as many as 3.2 million immature and adult CBBs per acre. Further, the CBBs within the berries remained reproductively active and continued to emerge for up to three months after being on the ground. In order to minimize the risk of existing populations continuing into the next season, all berries removed prior to pruning must either be buried or burned.

Coffee has a prolonged and variable fruiting season, flowering depends on several environmental conditions, berry growth is slow, and all berries do not ripen simultaneously. This poses an on-going challenge for coffee farmers attempting to intercept female CBBs as they emerge from their birth berry and seek out a new, uninhabited host berry. Traps, such as the BROCAP® (CIRAD, Paris, FR), can be installed at a rate of 8 per acre and suspended from the coffee tree at 1.5 m. Traps necessitate a lure composed of methanol and ethanol mixed to various ratios. Baited traps do not guarantee the removal of the CBB from the field, although at sufficient trap density protection can be achieved. More often traps are used in an effort to monitor for the presence of the beetle in the field.

During harvest, emphasis is placed on removing all ripe and dropped fruit. Harvest bags should be tied shut at harvest to avoid the escape and dispersal of CBB. The processing of berries to seeds should be performed in closed or semi-closed structures to prevent the escape of CBBs and allow for proper disposal. Additionally, during post harvest, dried and dropped berries should be collected from the field and buried or burned as they were at the beginning of the season.

There may exist alternative and/or more effective methods to control CBB. CBB, like most beetles, uses chemical signaling systems to determine many aspects of its life cycle. Semiochemicals, artificially or naturally sourced, can be used to influence these chemical pathways. One common function of these semiochemicals in beetle populations is repellency; communicating to incoming beetles that a particular host is overpopulated and no longer suitable for colonization.

CBB is a bark beetle and member of the sub-family Scolytidae. This sub-family includes a genus of beetles, *Dendroctonus*, that are well known major pests to global timber industries and as such have well researched and documented semiochemical communication systems. One semiochemical, verbenone, has shown to be strongly repellent to the *Dendroctonus* genus and may be strongly repellent to the entire Scolytidae sub-family.

Prior studies have shown that on average, CBB chose to travel down a path not containing verbenone. In these experiments a Y-tube olfactometer was used to force CBB to travel one of two paths in order to elucidate what impact, if any, specific semiochemicals, known to influence the behavior of other bark beetles, have on CBB. The results confirmed that verbenone is unattractive to CBB and can potentially be correlated, but not confirmed, to have a repellant effect. However, the study did not provide any specific information on the dosage or verbenone type used.

What was not previously known, and has been now discovered, is that exposure to (1S)-(-)-Verbenone (cas#1196-01-6), as well as other verbenone enantiomers will cause both male and female CBBs to dislodge from the coffee berry. The invention herein pertains to use of all potential verbenone sources, including synthetic sources, natural sources or any natural extract containing verbenone for the use of repelling or otherwise modifying the behavior of *Hypothenemus hampei*, the coffee berry borer. The present discovery applies specifically to the amount of verbenone, including all verbenone enantiomers, required to achieve such repellency. Applications of 1-10,000 g of verbenone (Active Ingredient, A.I.) per acre, using wax emulsions or any other field application technology, will be sufficient to repel CBB from a coffee field.

Verbenone has been discovered to be an efficacious repellant to CBB within a coffee plantation. The repellent effect will be used to push CBB from a currently infested plantation, decreasing or potentially removing the infestation within the application area. The technology disclosed herein may also be used to repel CBB and prevent its establishment in low or non-infested plantations, such as new plantings, aggressively controlled areas or geographic regions where CBB has not entered.

Another aspect of the presently disclosed invention is the use of verbenone as an accessibility tool. By repelling CBB from the coffee berries, CBB becomes accessible to insecticide sprays. Such an increase in accessibility will lead to more effective insecticide regimes and to a more efficient use of such insecticides.

It is believed that that 1-2,500 verbenone point sources per acre, using monolithic or any other field application technology, will provide effective repellency to CBB.

Based on the considerations above, verbenone acts as a suitable CBB repellent when formulated with the Specialized Pheromone and Lure Application Technology (SPLAT) described in U.S. Pat. No. 7,887,828, the entirety of which is incorporated by reference herein. This formulation for Coffee Berry Borer of the present invention (coined SPLAT Verb, and used as such herein) has a strong repellent effect on adult CBB, at low, economically viable doses; it is produced commercially and in large quantities, is labeled organic and registered for "all crops"; and it is a stable molecule (once UV-protected and anchored by SPLAT).

BRIEF SUMMARY

One embodiment of the present disclosure is directed toward systems and methods for controlling arthropod populations at the adult stage. The systems and methods of the present invention utilize repellents that are reactive upon an adult stage arthropod.

One embodiment of the present invention is directed toward a repellent system for controlling arthropod populations. The arthropods are characterized by a semiochemical-affected adult stage. The system of this embodiment includes a polymeric substrate and a semiochemical. The semiochemical is reactive upon the adult stage arthropod and is intermixed within the polymeric substrate. The semiochemical may be a pheromone, and may specifically be an anti-aggregation pheromone that disrupts the behavior of the adult arthropod.

The polymeric substrate may be present in numerous different configurations, including, but not limited to, microspheres, latex solutions, hot melt glues, resins, plastic flakes, and wax emulsions. The waxes that may be used in the wax emulsion include, but are not limited to, paraffin wax, carnauba wax, beeswax, candelilla wax, fruit wax, lanolin, shellac wax, bayberry wax, sugar cane wax, microcrystalline wax, ozocerite, ceresin, montan wax, and combinations thereof. The hot melt glues include, but are not limited to, glues including ethylene-vinyl acetate, polyethylene, polypropylene, a polyamide, or a polyester. One wax emulsion may be made up of 30% paraffin wax, 4% soy oil, 2% Span 60, 1% vitamin E, and distilled water. Another wax emulsion envisioned by the present invention includes 45% microcrystalline wax, 6% soy oil, 3% Span 60, 1% vitamin E, and distilled water.

The semiochemical may be dissolved within the polymeric substrate, including within wax emulsions. As discussed above, the semiochemical may be a pheromone, or more specifically, may be an anti-aggregation pheromone. One particular anti-aggregation pheromone that may be utilized is verbenone. When verbenone is used, it may be present in the system in a range between about 0.001% by weight to about 60.0% by weight. More particularly, the verbenone may be present in the system in an amount of about 10% by weight.

Although the system may be utilized to control the population of a wide range of arthropods, this embodiment is also well suited for controlling insect populations, and more particularly, coleopteran populations. The system may be in a fluid form conducive to use within conventional aerial spray equipment. The system may be prepared so as to release the semiochemical over a long period of time, for example, over a 2-6 month period.

Another embodiment of the present disclosure is directed toward a method for increasing the accessibility to control measures of an arthropod population in a region. The arthropod is characterized by having a semiochemical-affected adult stage. In this method, a system is administered to a region. As used herein, the region includes not only the orchard or plantation, but also the outer layers of individual trees, surrounding ground cover, gardens, and individual plants. The system administered to the region is of the type described above, that is, the system is made up of a polymeric substrate and a semiochemical. The semiochemical is reactive upon the adult stage of the arthropod and is intermixed within the polymeric substrate.

The system may be administered by aerial spray equipment. Furthermore, the system may be administered by conventional aerial spray equipment mounted on fixed-wing aircraft or rotorcraft. The system may also be administered by terrestrial-based methods. For example, the system may be administered by terrestrial-based spraying systems or by dispersing the system by way of "paintballs."

The method enables the novel effect of interfering with the behavior of the adult stage arthropod. As such, the method controls the population of the arthropod by interacting with the adult stage of the arthropod, causing them to become more accessible to control measures including but not limited to insecticides. Accordingly, the system may be administered during the immature stage of the arthropod and by being in the form of a controlled-release, rainfast, substance, the system remains present until the adult stage of the arthropod is reached. For example, in the case of controlling CBB populations, the system may be administered prior to coffee berry formation and the system may remain within the region for at least six months thereby being present during the entire life cycle of the CBB and being present to interfere with the adult-stage of the CBB. Accordingly, the semiochemical may repel any adult-stage CBB present, thereby removing the CBB from the berry and increasing accessibility to the CBB to better implement control measures.

As discussed above, the semiochemical may be a pheromone, or more particularly may be an anti-aggregation pheromone. One pheromone envisioned for use in the method is verbenone. One particular embodiment of the method includes administering the system to the region such that each hectare, or subparcel, of the region is administered 10 grams of verbenone.

Another embodiment of the present disclosure is directed toward a method of preparing a dispersible system for use in controlling the population of arthropods. The steps of this method include providing a polymeric substrate and adding a semiochemical to the polymeric substrate. The semiochemical is reactive upon an adult stage arthropod. Furthermore, the semiochemical may be a pheromone. In particular, the pheromone may be an anti-aggregation pheromone. One particular pheromone that may be utilized is verbenone. The polymeric substrate may be a wax emulsion. In this embodiment, the wax emulsion may be formed by melting a wax, adding an oil, emulsifier, preservative, and water heated above the melting temperature of the wax to the melted wax to form a wax emulsion, and cooling the wax emulsion. Although many waxes are contemplated, the waxes may include, but are not limited to, paraffin wax and microcrystalline wax. Additionally, the oil may be soy oil, the emulsifier may be Span 60, and the preservative may be vitamin E.

One embodiment of the present disclosure is directed toward methods for dislodging coffee berry borer from a coffee berry. The method involves administering a system on or in the vicinity of the coffee berry, wherein the system is made up of a polymeric or wax substrate and a semiochemical capable of affecting the coffee berry borer intermixed within the substrate. The substrate may be a wax emulsion, microspheres, a latex solution, hot melt glue, a resin, or plastic flakes. The semiochemical may be a pheremone, or more particularly an anti-aggregation pheremone. In particular, the anti-aggregation pheremone may be verbenone, methyl salicylate, an extract and infusion from the botanical orders Alismatales, Apiales, Arecales, Asparagales, Asterales, Brassicales, Canellales, Caryophyllales, Cycadales, Dipsacales, Ericales, Fabales, Gentianales, Lamiales, Laurales, Magnoliales, Malpighiales, Malvales, Myrtales, Pinales, Poales, Ranunculales, Rosales, Sapindales, Solanales, Theales or Zingiberales, or combinations of any thereof.

When the anti-aggregation pheremone is verbenone, it may be (−) Verbenone, (S) Verbenone, Levobernone, L-Verbenone and its respectives isomers: (+) Verbenone, (R) Verbenone, D-Verbenone or any Verbenone containing isotopes of hydrogen (deuterium) and Carbon (13 Carbon) at any position in its structure. The verbenone may be present in the system in a range between about 0.001% by weight to about 60.0% by weight. In certain embodiments, the verbenone is present in the system in an amount of about 10% by weight.

The system may be administered by either aerial spray equipment mounted on fixed-wing aircraft or rotorcraft or by a terrestrial-based spraying system, and may be administered such that each hectare containing coffee berries is administered 1-10,000 g of the semiochemical per hectare. In certain embodiments, each hectare containing coffee berries is administered 4,400 g of the semiochemical per hectare.

Another embodiment of the present disclosure is directed toward methods of repelling arthropods in a region. The method features administering a system to the region, wherein the system has a polymeric or wax substrate and an anti-aggregation pheremone intermixed within the substrate. The substrate may be a wax emulsion, microspheres, a latex solution, hot melt glue, a resin, or plastic flakes. The anti-aggregation pheremone may be verbenone, methyl salicylate, an extract and infusion from the botanical orders Alismatales, Apiales, Arecales, Asparagales, Asterales, Brassicales, Canellales, Caryophyllales, Cycadales, Dipsacales, Ericales, Fabales, Gentianales, Lamiales, Laurales, Magnoliales, Malpighiales, Malvales, Myrtales, Pinales, Poales, Ranunculales, Rosales, Sapindales, Solanales, Theales or Zingiberales, or combinations of any thereof.

The method may be used to repel insects, and more particularly coleopterans. Indeed, it is envisioned that the method may be used to repel coleopteran from the genera: *Dendroctonus* spp., *Rhynchophorus* spp., *Hypothenemus* spp., and *Xylosandrus* spp. The method is envisioned to particularly work to repel the coffee berry borer.

Yet another embodiment of the present disclosure is directed toward systems for repelling coffee berry borer. The system includes a polymeric or wax substrate and an anti-aggregation pheromone intermixed within the substrate. The substrate may be a wax emulsion, microspheres, a latex solution, hot melt glue, a resin, or plastic flakes. The anti-aggregation pheromone may be verbenone, methyl salicylate, an extract and infusion from the botanical orders Alismatales, Apiales, Arecales, Asparagales, Asterales, Brassicales, Canellales, Caryophyllales, Cycadales, Dipsacales, Ericales, Fabales, Gentianales, Lamiales, Laurales, Magnoliales, Malpighiales, Malvales, Myrtales, Pinales, Poales, Ranunculales, Rosales, Sapindales, Solanales, Theales or Zingiberales, or any combinations thereof.

The system may further include an insect toxicant. The substrate may be a wax emulsion formed by melting a wax and adding to the melted wax, an oil, an emulsifier, a preservative, and water heated above the melting temperature of the wax to form the wax emulsion. The wax emulsion is then cooled. In one particular embodiment, the system has the formula shown in Table 1 below.

TABLE 1

| water | 5%-60% by weight; |
|---|---|
| petrolatum | 2%-20% by weight; |
| soybean oil | 5%-80% by weight; |
| sorbitan monostearate | 0.1%-10% by weight; |
| fumed silica | 0.5%-10% by weight; |
| wax | 1%-50% by weight; |
| activated charcoal | 0.1%-5% by weight; |
| verbenone | 1%-60% by weight; and |
| methyl salicylate | 1%-60% by weight. |

Alternatively, the wax emulsion may be made up of a wax carrier selected from paraffin wax, carnauba wax, beeswax, candelilla wax, fruit wax, lanolin, shellac wax, bayberry wax, sugar cane wax, microcrystalline wax, ozocerite, ceresin, montan wax, or combinations thereof. One particular embodiment has a wax emulsion with the components listed in Table 2.

TABLE 2

30% by weight paraffin wax;
4% by weight soy oil;
2% by weight sorbitan monostearate
1% by weight vitamin E; and
58% by weight distilled water.
The system of claim 3, wherein the wax emulsion comprises:

45% by weight microcrystalline wax;
6% by weight soy oil;
3% by weight sorbitan monostearate;
1% by weight vitamin E; and
40% by weight distilled water.

The substrate may alternatively be a hot melt glue, in particular it may be a polymer selected from ethylene-vinyl acetate, polyethylene, polypropylene, a polyamide, or a polyester.

The formulations described above may further include water, wherein the wax carrier is in a fluid suspension of the water. The fluid suspension may be an emulsion. The formulations may further include one or more additives selected from lipids, emulsifiers, plasticizers, UV blockers and absorbers, antimicrobials, antioxidants and volatility suppressants. These additives, if present, may be in an amount from about 0.001% to about 20% by weight. The emulsifiers may be lipids, soy oil, lecithins, modified lecithins, monoglycerides, diglyceridies, sorbitans, fatty acids, or combinations thereof. The emulsion may be sprayable, squirtable or spreadable.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
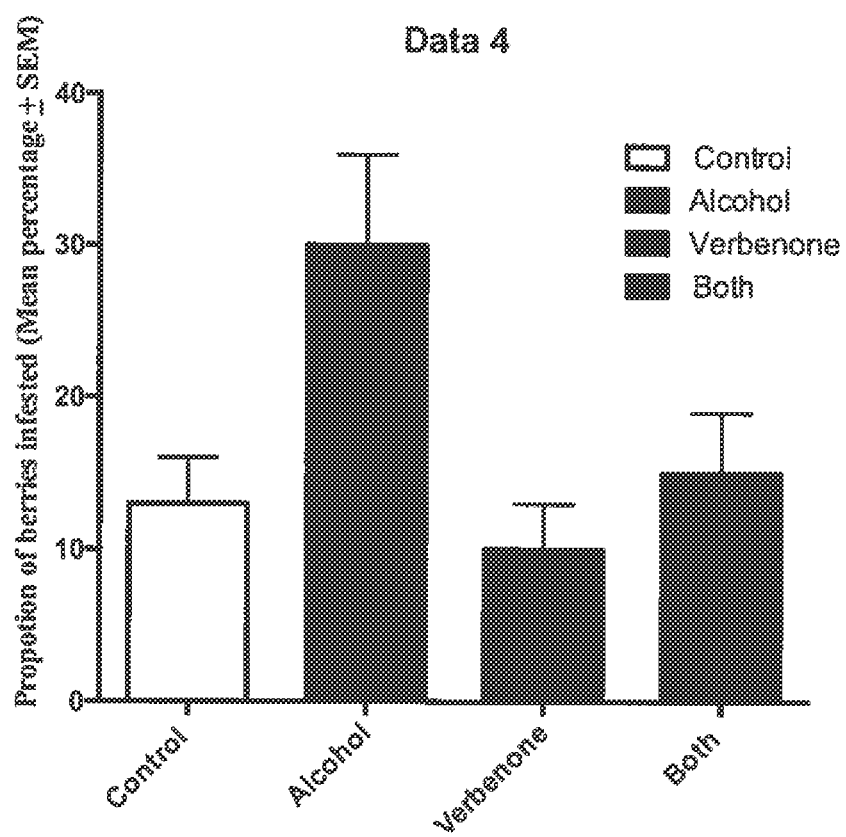
FIG. 1 is a graph showing coffee berry infestation between control groups and those being treated with a composition as described herein.

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Semiochemical formulations should exhibit a zero-order-release rate and sustain release levels above a certain threshold for a long period of time, wherein release levels below threshold would only have a negligible disruptive effect on the behavior of the target insect. With a couple of exceptions, when formulated with less than 10% active ingredient (AI) Specialized Pheromone and Lure Application Technology (SPLAT) consistently provides a near zero-order-release rate of the semiochemical, with negligible flash-off around the time of application.

The initial research and development that culminated into the existing SPLAT technology was done using *Grapholita molesta*, the Oriental fruit moth (OFM), a serious pest of apples worldwide, as the model insect. When formulated with less than 10% OFM pheromone, SPLAT consistently provided a near zero-order-release rate with negligible flash-off. Field trials in large commercial apple operations in South America indicated that SPLAT formulations containing 15 g pheromone per acre sustained nearly complete trap shutdown for over 180 days, which actually translated in a significant reduction of OFM fruit damage, as compared to that found in the grower's traditional chemical control. Analysis of the field "aged" SPLAT indicated that there were different levels of pheromone remaining in the point source of SPLAT by the end of the 180 day trial period, and it was related to the position of the dollop in the canopy (receiving more or less solar incidence) as well as the actual size of the dollop analyzed: pheromone in microdollops was undetectable, whereas 1 g dollops still contained 5-10% and 5 to 10 g dollops retained between 10 and 25% AI.

In the case of CBB, the present disclosure envisions a SPLAT and pheromone based repellent formulation that provides acceptable long-term repellency while minimizing any potential deleterious impacts. The application of SPLAT and verbenone can occur at the onset of coffee berry formation and by remaining in place emitting pheromone would repel existing and emerging adults from further damaging developing coffee berries.

This novel formulation, a SPLAT and verbenone formulation that is repellent, can be applied using conventional defensive application apparatus, will last for 6 months or longer in the field, releases nearly all the pheromone it contains, and is biodegradable and safe.

This formulation provides coffee farmers with a functional system and substantial savings. The cost of SPLAT with 10 g verbenone/acre will be about $30 dollars per acre, which represents a savings of $30-60 per acre just considering the cost of BOTANIGARD® ES. Now, if this formulation also substitutes the customary two treatments of BOTANIGARD® ES at a cost of $60-90/acre, then the savings will be $60-120/acre.

Our calculation of the savings is very conservative. It does not take in account the additional savings realized because of the simplification of the current cultural control CBB operation, a formulation with such a long life that it allows for a single application for the entire CBB cycle. More savings will be achieved by elimination of crisis situations and their associated cost. Furthermore, we believe we overestimate the cost of manufacturing SPLAT. It is probably high because it is based on the price we currently pay our suppliers, which do not reflect the discounts available from commercial suppliers when we purchase the raw materials in large bulk quantities. Furthermore the efficiency of the production line increases with the larger volumes, needing less worker hours per volume of SPLAT produced. These additional savings have not been accounted for.

Because of its repellent action, SPLAT and verbenone may provide population protection not only in areas of existing populations but also areas with low and no population densities, such as newly established plantations, providing a huge benefit to the coffee industry and population in general.

It is believed that the ideal verbenone formulation should be applied using conventional spray equipment, have a duration of at least two to six months, stick to the foliage where it lands, quickly acquire rain-fast qualities, protect the pheromone from degradation, work synergistically with adulticides so that it can possibly control CBB populations at low as well as at high densities, be biodegradable, if possible organic, not damage private property, and last but not least the formulation should be inexpensive for its adoption to be not only technically, but also economically feasible.

The present invention is expected to meet all of the desired factors by providing an optimal semiochemical solution for the effective management of CBB independent of population density. The overall objective of this invention is to provide effective season-long field control of CBB populations using a flowable wax emulsion system (SPLAT) that delivers the anti-aggregation pheromone verbenone. We formulated SPLAT and verbenone using flowable wax emulsions of different characteristics in order to determine in the lab the emission rate and stability of the pheromone. Two of the optimized formulations were submitted to laboratory and field trials to which we added high CBB pressure. Field aged samples of the SPLAT formulations were analytically quantified to determine residual stability and effectiveness of pheromone components.

Some of the goals of the invention include: 1) a formulation having a duration of six months while being protected from degradation while dispensing verbenone; 2) a formulation that works synergistically with killing agents; 3) a formulation of SPLAT that works with conventional aerial spray equipment, sticks to foliage and quickly becomes rain-fast; and 4) a formulation that controls CBB populations at low as well as high densities. However, it is contemplated that in some embodiments of the invention only some, or even none of the goals may be achieved.

There are no verbenone formulations in the market today that have high longevity and that can be applied using conventional spray equipment. The present invention is an optimal semiochemical solution for the effective management of CBB independent of population density. The present invention is effective in season-long field control of CBB populations using a flowable wax emulsion system (SPLAT) that delivers the anti-aggregation pheromone verbenone. The release rate of verbenone from SPLAT, 10% of pheromone in the SPLAT composition, applied in the field as point sources at three sizes, 1 g, 7 g and 17 g each was measured. The SPLAT formulations retained and continued emitting pheromone for 120 days, with the formulations still retaining 30%-80% of its pheromone (depending on dose and point source size). This suggests that these formulations would probably last another 30 to 60 days in the field (depending on dose and point source size). This indicates that if the formulation is sprayed in the field at the time of coffee berry development, it will last through harvest. This allows for the first time a formulation that can be sprayed to control CBB through the emission of effective rates of pheromone during adult flight.

By targeting CBB with an organic, safe, and effective formulation, non-target organisms will be minimally affected by any extra insecticide use, so insect species diversity will be retained where the semiochemical formulation is used. This in turn will conserve vertebrate animals that depend upon insects for their diet.

In one embodiment of SPLAT and verbenone the pheromone lasts for the whole season, but just for the coffee berry production season, not longer, to avoid unwanted residual problems and exposure to non-target species. The systems and methods of the present invention may be utilized for a plethora of other pests and invasive species (e.g., Mountain Pine Beetle, Southern Pine Beetle, Western Pine Beetle and others).

Our testing involved application of approximately 0.2 g of SPLAT Verb in approximately a 6-inch petri dish. (SPLAT Verb is loaded with 10% verbenone by weight.) This area would correspond to 0.0000045 ac of land; therefore, our field application rate would be approximately 44 kg of SPLAT Verb (4,400 g of verbenone) per acre. Coffee berries, commonly used to rear CBB, were placed in the petri dish. The 0.2 g of SPLAT Verb was introduced into the sealed petri dish. We then went on to measure the times when CBB dislodged or exited the berry. The number dislodged is a summation of the total dislodged at that point in time. Our data (as shown in Table 3) verifies that CBB exited their preferred host and, after dislodging, maintained high activity levels without re-entering the berries. This data serves as the first confirmation of verbenone's repellant activity.

TABLE 3

| Time | Number Dislodged | Activity Level Outside of Berry |
|---|---|---|
| 4 min 51 sec | 2 | High |
| 7 min 17 sec | 3 | High |
| 15 min 32 sec | 4 | High |
| 19 min 25 sec | 6 | High |
| 22 min 21 sec | 7 | High |
| 28 min 38 sec | 8 | High |
| 32 min 32 sec | 9 | High |
| Total in 37 min | 9 | High |

Figure 2:
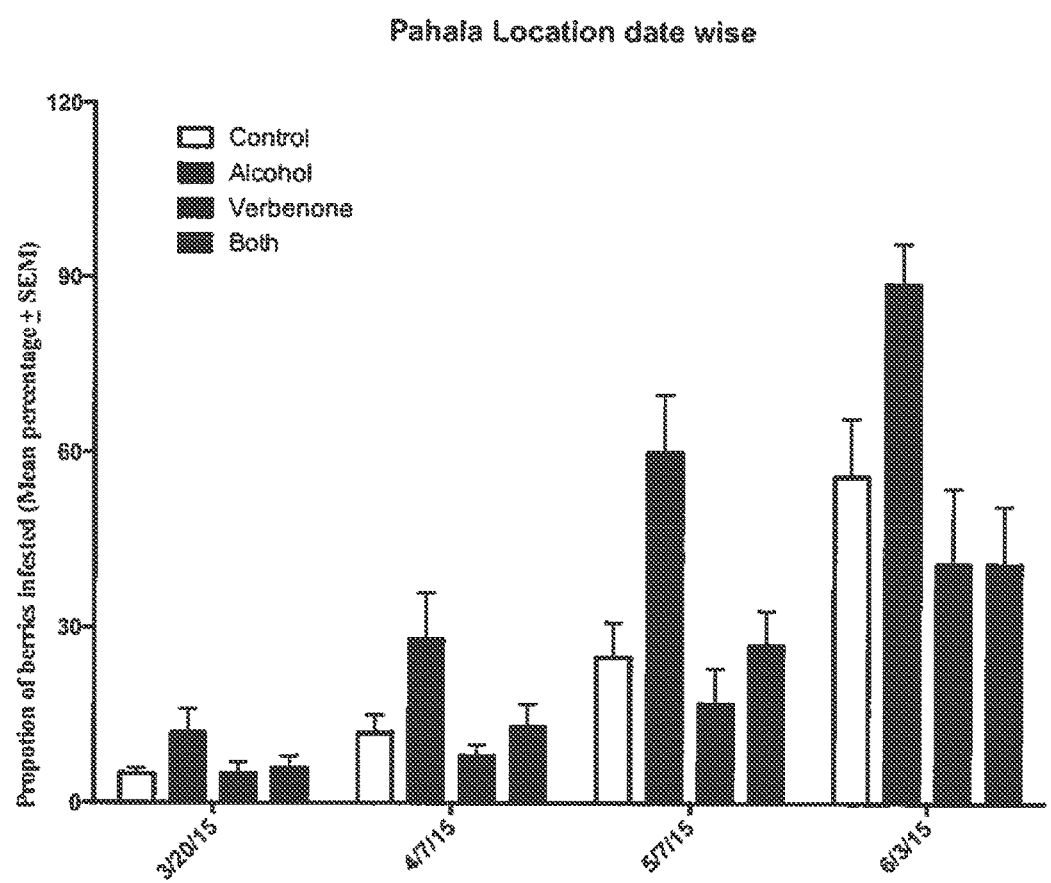
FIG. 2 is a graph showing coffee berry infestation as described in FIG. 1 over a period of time.

Alcohol is a strong CBB attractant. Further testing of SPLAT Verb shows (as can be seen in FIGS. 1 and 2) that the addition of verbenone reduces the level of attraction of CBB even to traps with alcohol to levels below the control (trap without attractant or any other semiochemical).

The SPLAT and verbenone pheromone release formulation, a novel, amorphous, flowable emulsion can be applied as microliter point sources all the way to dollops of tens of grams. The SPLAT wax dispenser formulations of this invention belong to a "matrix-type" or "monolithic" category of controlled-release devices. These "matrix-type" or "monolithic" dispensers are defined as devices where the active ingredient is dispersed or dissolved in a polymer matrix. Release of the active ingredient from a monolithic device occurs by diffusion and can be described macroscopically by Fick's Law. Fick's law states that the movement of a molecule by diffusion is directly proportional to the concentration of that molecule in a system. Microscopically, if we follow the movement of a molecule of an active agent through a matrix, this molecule can begin its journey in one of two ways. If it is dispersed in the matrix, it begins its journey by dissociating from other molecules in its crystal cell and solubilizing into the polymer phase. If it is dissolved in the matrix, then this step is bypassed. The molecule then diffuses through amorphous regions in the matrix that comprise the free volume of the system. The molecule can move through the matrix in one of two ways as well. If it is very small compared to the size of the amorphous spaces in the matrix, then it will diffuse through the matrix by moving from one such space to another. If it is very large compared to the size of those spaces, then segments of the polymer comprising the matrix will have to be rearranged for diffusion of the active agent molecule to occur. Crystalline regions in the matrix are virtually impermeable to molecules of the active agent. Upon reaching the surface of the matrix, it will be released into the environment.

A series of factors influences the rate of release of an active agent from a monolithic device and includes properties of the matrix material as well as properties of the active agent. The temperature of the matrix influences release of the active agent; at higher temperatures the free volume is increased, and diffusion occurs faster. At lower temperatures, the free volume is decreased, and diffusion is slower. The thermal history of a polymer can also increase or decrease the free volume of the system and lead to changes in the diffusional rate of an active agent.

The property of the active agent having the greatest influence on its release rate is its molecular weight. Generally, larger molecules take more time to make their way through the free space of a matrix. Branching in a molecule can also decrease its rate of diffusion through a matrix. The partition coefficient of the active agent between the matrix and the environment can also influence the release rate of that agent. If the agent readily partitions to the environment, then its rate of release will be diffusion-controlled and first order. If, however, partitioning of the active agent to the environment is relatively slow, then its partition coefficient will determine its release rate from the matrix and the device will exhibit zero order release kinetics. The partitioning of the active agent to the environment is a function of the solubility of the active agent in the matrix; compounds more soluble in the matrix partition to the environment more slowly. SPLAT paraffin emulsions in a field environment exhibit diffusion-controlled release. The surface area of the device also influences its release rate. Paraffin dispensers with larger surface areas release active agent at faster rates.

The release rate of a SPLAT formulation containing a fixed amount of semiochemical can be modulated simply by changing a few of parameters of the formulation, which includes the type of components used (e.g. the wax composition, the emulsifiers used), their proportion in the formulation (e.g., percentage of water, oil or wax content), the stage in the manufacturing the different components are added, the rheology, and finally the characteristics of application of the SPLAT in the field (e.g., applied as microdollops of 1-10 ug each or large dollops of 10 g each).

The result is a semiochemical formulation that is extremely malleable and that fits many needs and uses that cannot be supported by any other commercial formulation present in the market.

A 30% paraffin wax emulsion was made consisting of 30% paraffin wax (Gulf Wax, Royal Oak Sales, Inc., Roswell, Ga.), 4% soy oil (Spectrum Naturals, Inc., Petaluma, Calif.), 2% Span 60 (Sorbitan monostearate, Sigma-Aldrich Co., St. Louis, Mo.), 1% vitamin E α-tocopherol, Sigma Chemical Co., St. Louis, Mo.), and 58% distilled water. A 45% microcrystalline wax emulsion consisting of 45% microcrystalline wax (Blended Waxes, Inc., Oshkosh, Wis.), 6% soy oil, 3% Span 60, 1% vitamin E, and 40% distilled water was also made.

The wax is melted (paraffin: 60-65° C.; microcrystalline: 78-80° C.) and water heated above the melting temperature of the wax (paraffin emulsion: 65-70° C.; microcrystalline emulsion: 78-88° C.). The soy oil, Span 60, and vitamin E are added to the melted wax and thoroughly mixed, followed by the addition of the hot water. This mixture is then poured into a industrial laboratory blender. The emulsion is immediately blended, then placed in a cold water bath, and mixed every 15 minutes until the solution had cooled to 25-30° C. when it is placed in a plastic bucket and stored until use.

Just prior to use, 0.03% (3 g), 1.0% (10 g) and 3.0% (30 g) by weight of emulsion of racemic verbenone is thoroughly mixed into the emulsion using a high sheer lab mixer.

Preliminary work with generic SPLAT formulations containing 3% racemic verbenone using flow cells indicates that it releases pheromone at a very constant level for long periods. To show the release of AI semiochemicals within SPLAT, we collected the effluvia from 5 g SPLAT GM 3%, containing 150 mg disparlure (AI) and found that it released disparlure at a rate of 44.06±13.08 ug/day for over ca. 170 days. As a comparison, 5 g of Disrupt II (a prior art formulation), containing 894 mg disparlure emit 51.45±2.33 ug/day. It is important to realize that although both flow chambers had 5 grams of formulation, Disrupt II actually had six times more pheromone than SPLAT while it released only 15% more pheromone than SPLAT, a difference that probably has no biological effect to speak of. These results suggest that SPLAT is a much more efficient formulation than those known in the prior art; actually six times more efficient. As such, one would need to apply six times less AI using SPLAT than if using prior art formulations. Usually the most expensive component of a mating disruption formulation is the active ingredient. Accordingly, SPLAT is believed to be substantially less expensive than the formulations of the prior art.

With SPLAT, one can change the consistency of the emulsion by changing the proportion of components, or by changing the rheology of the mixing of the components. The word "rheology" normally refers to the flow and deformation of "non-classical" materials such as rubber, molten plastics, polymer solutions, slurries and pastes, electrorheological fluids, blood, muscle, composites, soils, and paints. These materials can exhibit varied and striking external and internal structures due to their rheological properties that classical fluid mechanics and elasticity cannot describe. Our experience is that the SPLAT formula with 45% microcrystalline wax emulsion (45% microcrystalline wax, 6% soy oil, 3% Span 60, 1% vitamin E, and 40% distilled water) can be mechanically applied and that it adheres quickly to the vegetation, and as long as it has a couple hours to settle, it becomes rain fast.

Specialized Pheromone & Lure Application Technology (SPLAT) is a base matrix formulation of biologically inert materials used to control the release of semiochemicals and/or odors with or without pesticides. Extensive research on SPLAT using a variety of lures demonstrates that this matrix emits semiochemicals at effective pest suppression levels for a time interval ranging from 2-16 weeks. Having a wide range of viscosities and application methods (e.g. applicator sprays, aerial applicator sprays, caulking gun type tubes, etc.), SPLAT increases productivity by mechanizing the application of pheromone dispensing points. The amorphous and flowable quality of this highly adaptable product allows for an easy transition from small-scale manual applications to large-scale mechanical applications.

The above description is given by way of example, and not limitation. Given the above disclosure, one skilled in the art could devise variations that are within the scope and spirit of the invention disclosed herein, including various ways of administering the verbenone. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method for dislodging coffee berry borer from a coffee berry, the method comprising administering a system on or in the vicinity of the coffee berry, the system comprising:

a polymeric or wax substrate selected from the group consisting of a wax emulsion, microspheres, a latex solution, hot melt glue, a resin, and plastic flakes; and verbenone in an amount sufficient to dislodge the coffee berry borer from the coffee berry intermixed within the substrate;

wherein the system will last for at least about six months once administered.

2. The method of claim 1, wherein the verbenone is selected from the group consisting of (−) Verbenone, (S) Verbenone, Levobernone, L-Verbenone and its respectives isomers: (+) Verbenone, (R) Verbenone and D- Verbenone and any Verbenone containing isotopes of hydrogen (deuterium) and Carbon (13Carbon) at any position in its structure.

3. The method of claim 1, wherein the verbenone is present in the system in a range between about 0.001% by weight to about 60.0% by weight.

4. The method of claim 3, wherein the verbenone is present in the system in an amount of about 10% by weight.

5. The method of claim 1, wherein the system is administered by either aerial spray equipment mounted on fixed-wing aircraft or rotorcraft or by a terrestrial-based spraying system.

6. The method of claim 5, wherein the system is administered such that each hectare containing coffee berries is administered 1-10,000g of verbenone per hectare.

7. The method of claim 6, wherein the system is administered such that each hectare containing coffee berries is administered 4,400g of verbenone per hectare.

8. A method for dislodging coffee berry borers from coffee berries within a region, the method comprising administering a system to the region, the system comprising:

a polymeric or wax substrate selected from the group consisting of a wax emulsion, microspheres, a latex solution, hot melt glue, a resin, and plastic flakes;

an insect toxicant within the substrate; and verbenone in an amount sufficient to dislodge the coffee berry borer from the coffee berry within the substrate, wherein the system will last for at least about six months once administered.

9. A system for dislodging coffee berry borers from coffee berries, the system comprising:

a polymeric or wax substrate selected from the group consisting of a wax emulsion, microspheres, a latex solution, hot melt glue, a resin, and plastic flakes; and verbenone intermixed within the substrate.

10. The system of claim 9, further comprising an insect toxicant.

11. The system of claim 9, wherein the substrate is a wax emulsion formed by:

melting a wax; and adding to the melted wax, an oil, an emulsifier, a preservative, and water heated above the melting temperature of the wax to form the wax emulsion.

12. The system of claim 11, comprising:

| | |
|---|---|
| water | 5%-60% by weight; |
| petrolatum | 2%-20% by weight; |
| soybean oil | 5%-80% by weight; |
| sorbitan monostearate | 0.1%-10% by weight; |
| fumed silica | 0.5%-10% by weight; |
| wax | 1%-50% by weight; |
| activated charcoal | 0.1%-5% by weight; |
| verbenone | 1%-60% by weight; and |
| methyl salicylate | 1%-60% by weight. |

* * * * *